(12) United States Patent
Saweres Mina

(10) Patent No.: US 12,708,746 B2
(45) Date of Patent: Aug. 18, 2026

(54) ACCESS AND TREATMENT CATHETERS FOR ENDOVASCULAR PROCEDURES

(71) Applicant: Ayman Gerges Saweres Mina, Dubai (AE)

(72) Inventor: Ayman Gerges Saweres Mina, Dubai (AE)

(73) Assignee: Piezolabs Medical Inc., Lake Forest, CA (US)

( * ) Notice: Subject to any disclaimer, the term of this patent is extended or adjusted under 35 U.S.C. 154(b) by 442 days.

(21) Appl. No.: 18/370,804

(22) Filed: Sep. 20, 2023

(65) Prior Publication Data

US 2024/0238561 A1 Jul. 18, 2024

Related U.S. Application Data

(60) Provisional application No. 63/468,202, filed on May 22, 2023, provisional application No. 63/445,777, filed on Feb. 15, 2023, provisional application No. 63/439,077, filed on Jan. 14, 2023.

(51) Int. Cl.
*A61M 25/01* (2006.01)

(52) U.S. Cl.
CPC . *A61M 25/0158* (2013.01); *A61M 2205/0294* (2013.01)

(58) Field of Classification Search
CPC ................ A61B 2017/00318; A61M 25/0158
See application file for complete search history.

(56) References Cited

U.S. PATENT DOCUMENTS

| | | | |
|---|---|---|---|
| 5,281,215 | A | 1/1994 | Milder |
| 5,415,633 | A | 5/1995 | Lazaus |
| 5,771,902 | A | 6/1998 | Lee et al. |
| 6,361,500 | B1 | 3/2002 | Masters |
| 7,172,552 | B2 | 2/2007 | Wendlandt |
| 7,608,056 | B2 | 10/2009 | Kennedy, II |
| 7,833,191 | B2 | 11/2010 | Flach et al. |
| 7,879,004 | B2 | 2/2011 | Seibel et al. |
| 8,551,041 | B2 | 10/2013 | Friend |
| 9,931,134 | B2 | 4/2018 | Hissong et al. |
| 10,058,235 | B2 | 8/2018 | Gunday et al. |

(Continued)

FOREIGN PATENT DOCUMENTS

| | | | | |
|---|---|---|---|---|
| FR | 2732225 A1 | 10/1996 | | |
| WO | WO-9817190 A2 * | 4/1998 | ........ | A61M 25/0158 |

(Continued)

OTHER PUBLICATIONS

International Search Report dated Apr. 26, 2024 for corresponding PCT Application No. PCT/IB2023/000788.

*Primary Examiner* — William R Carpenter
(74) *Attorney, Agent, or Firm* — Raymond Sun

(57) ABSTRACT

A catheter and a method of advancing the catheter within a human vessel are provided. The catheter has a shaft that has a distal end and a proximal end, a hub provided at the proximal end, and a first piezoelectric element provided at the hub. A second piezoelectric element is provided at a location on the shaft that is distal to the hub, and a conductive wire connects the first piezoelectric element and the second piezoelectric element. Electrical energy is applied from the first piezoelectric element towards the second piezoelectric element to cause the distal end of the shaft to move.

4 Claims, 6 Drawing Sheets

(56) References Cited

U.S. PATENT DOCUMENTS

| | | | | |
|---|---|---|---|---|
| 10,743,989 | B2 | 8/2020 | Quill et al. | |
| 11,013,554 | B2 | 5/2021 | Coates | |
| 11,617,860 | B2 | 4/2023 | Erkamp et al. | |
| 2005/0085693 | A1 | 4/2005 | Belson et al. | |
| 2012/0123326 | A1 | 5/2012 | Christian et al. | |
| 2013/0274712 | A1* | 10/2013 | Schecter ................ | A61B 34/76 604/100.01 |
| 2014/0214010 | A1 | 7/2014 | Kuo et al. | |
| 2015/0327922 | A1 | 11/2015 | Dawood et al. | |
| 2016/0001044 | A1* | 1/2016 | Rauch ............... | A61M 25/0158 606/108 |
| 2020/0345987 | A1* | 11/2020 | Jalgaonkar .......... | A61M 25/005 |
| 2021/0023348 | A1 | 1/2021 | Kaneka | |
| 2021/0162179 | A1 | 6/2021 | Cazeneuve et al. | |
| 2021/0353920 | A1 | 11/2021 | Braeuer | |
| 2022/0387106 | A1 | 12/2022 | Cook | |

FOREIGN PATENT DOCUMENTS

| | | | |
|---|---|---|---|
| WO | WO2008073126 | A1 | 6/2008 |
| WO | WO2020/170582 | A1 | 8/2020 |
| WO | WO2022177792 | A1 | 8/2022 |

* cited by examiner

ACCESS AND TREATMENT CATHETERS FOR ENDOVASCULAR PROCEDURES

BACKGROUND OF THE INVENTION

1. Field of the Invention

The present invention is directed to catheters and methods for accessing the human vasculature during endovascular procedures for the treatment of medical conditions in the blood circulation system.

2. Description of the Prior Art

Medical conditions causing reduced or stopped blood flow in the human vasculature can be dangerous, and in particular, if this happens in the neurovasculature, can lead to stroke, which is life threatening. There are a number of treatment devices available to treat the reduced blood flow by the blockages (recanalization procedures) or hemorrhage in the vasculature, but one must first make sure that the treatment devices can arrive at the target location through the access catheter in the vasculature in a safe, reliable and expedient manner. This means that the access catheter first has to be placed in the target location in the vasculature in a safe, reliable and expedient manner. In addition, access catheters and therapeutic catheters used in the treatment need to be navigated to more distal locations in the vasculature, for example, the M2 and M3 segments in the neurovasculature. Unfortunately, existing catheters do not satisfy all the above requirements.

A wide range of access devices and techniques are often used during the recanalization procedures in order to achieve a successful procedure. These include long sheaths, guide wires, diagnostic catheters, balloon guide catheters, a wide range of access catheters (e.g., intermediate catheters, microcatheters, distal support catheters, etc.), treatment catheters, and treatment devices such as stents, flow divertors, coils, intravascular devices, aspiration catheters, etc. The use of long sheaths, wires, access catheters and similar devices typically require extended time to accomplish the treatment. Therefore, it is critical to have a series of access catheters with superior performance to make the procedure simpler (i.e., fewer steps), faster (e.g., fewer maneuvers at each step), and safer (less traumatic).

Among the shortcomings experienced by the access and treatment catheters include excessive maneuvering needed to navigate through tortuous vasculature, excessive trauma to the vasculature, difficulty to access distal locations in the vasculature, and sacrificed lumen size for navigability (i.e., having a smaller lumen size to navigate further), among others. For example, existing aspiration catheters for clot removal cannot be delivered to near the proximal location of the blood clots for improved aspiration effect.

All of above shortcomings for the existing catheters result in the following problems. First, certain medical conditions cannot be treated if the location is too distal or the vasculature is too complicated in tortuosity. Second, prolonged procedure time can lead to excessive exposure in X-ray for both health care professionals and the patient. Third, prolonged procedure time can also lead to the delay in treatment resulting in poor post-procedure clinical outcome, especially for stroke patients, since every second of time delay results in the death of a greater number of brain cells. Fourth, excessive maneuvering and too many procedural steps create more damage to the vasculature, especially in the neurovasculature.

Thus, there is still a need for catheters that overcome the shortcomings outlined above, and which have improved trackability, pushability, torquability, and optimal stiffness distribution along the catheter shaft, and less-complicated tip structure and catheter material and structure design.

SUMMARY OF THE DISCLOSURE

The present invention provides a catheter and a method of advancing the catheter within a human vessel. The catheter has a shaft that has a distal end and a proximal end, a hub provided at the proximal end, and a first piezoelectric element provided at the hub. A second piezoelectric element is provided at a location on the shaft that is distal to the hub, and a conductive wire connects the first piezoelectric element and the second piezoelectric element. Electrical energy is applied from the first piezoelectric element towards the second piezoelectric element to cause the distal end of the shaft to move.

The catheter and method of the present invention can include both catheters for gaining the access to the target location in the vasculature (e.g., access catheters) and the catheters for treatment (treatment catheters/devices), such as for thrombus and emboli removal. The endovascular procedures cover neuro intervention, peripheral intervention, and coronary intervention, among others.

The present invention provides benefits that include: quicker and improved access to hard-to-reach target locations in the vasculature; less trauma to the vessel walls; the ability to reach more distal vasculature.

DETAILED DESCRIPTION OF THE PREFERRED EMBODIMENTS

Figure 1:
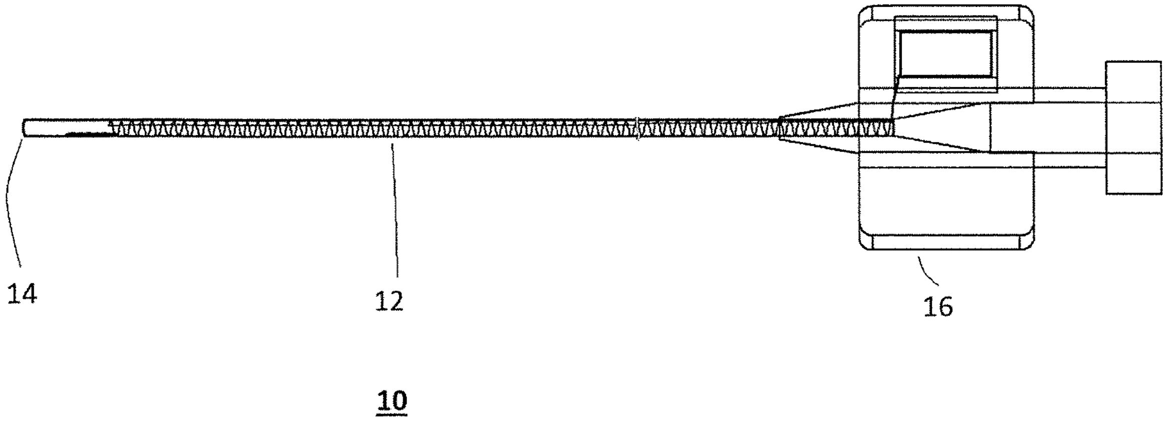
FIG. 1 is a schematic view of a catheter according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Before describing the embodiments of the present invention, a short description of existing catheter constructions would provide helpful context to understanding the principles of the present invention. Conventional catheters are typically constructed using a number of materials, and have various structures and/or layers within the catheter wall structure to control catheter performance.

One typical construction for existing catheters includes an outer layer that is made from various polymer materials having different durometers or stiffness. A reinforcement structure can be integrated into the catheter shaft and is usually made from either a braided, a coiled, or a combined braided and coiled structure, to control torquability/stiffness characteristics of the catheter at selected locations thereof. The construction also includes an inner liner or layer made from polymer materials to make the inner luminal surface smooth and to reduce friction when other access or treatment devices are passed through the lumen defined by the inner liner. A surface coating can be provided on either the outer diameter of the catheter only, or on both the inner diameter and the outer diameter surfaces for improved lubricity. Marker bands or other forms of radiopaque materials are also provided along the catheter shaft for visibility and to help for device positioning. Thus, existing catheter design mainly relies on the pure mechanical design/construction to control the characteristics of the catheter. In the practical application, a physician still needs to determine specific techniques for maneuvering the catheter shaft in order to advance the catheter. For example, the physician needs to form the shape of the catheter tip, push, pull, or rotate/twist at the bends, decide which support devices are to be used in the inner lumen, and operate multiple access devices at the same time.

The catheter design and method disclosed in the present invention includes one or more "functional element(s)" in the catheter construction. The "functional element" is made from piezo-electric materials. Piezo-electric materials are materials that have piezo-electricity. Piezoelectricity is the effect of mechanical strain/deformation and electric fields/potential on a material. Mechanical strain/deformation on piezoelectric materials will produce a polarity/potential in the material, and applying an electric field/potential to a piezoelectric material will create strain/deformation/bend within the material. When pressure is applied to a piezo-electric material, a dipole and net polarization/potential are produced in the direction of the applied stress/deformation. Piezoelectricity converts different types of energy into another type of energy. In the present invention, the conversion between the mechanical energy/deformation/bend to electricity/potential is used.

The present invention uses this piezo-electric effect to either convert the electric energy to mechanical strain/deformation, and/or convert the mechanical strain/deformation to electric energy, so that the catheter can experience bending motion to move "like a snake" through a patient's vasculature, thereby making the navigation easier, faster, less traumatic, and capable of extending further distally. The catheter design of the present invention also makes it possible for a catheter having a larger lumen to extend more distally in the vasculature.

The piezo-electric materials can be either piezo-electric ceramic and some ferroelectric materials (for example $BaTiO_3$, etc.), or piezo-electric polymer materials (for example, polyvinylidene fluoride, etc.), or the combination of the different types of piezo-electric materials (composite materials). The piezo-electric materials can be in the form of layers, sheet, tubular, thin film, surface layer, deposited or plated layer, printed layer, powder form, fibers, wires, textile/fabric, strip form, electrospun fibers, electrospun nanofibers, etc.

The piezo-electric materials can be incorporated in the catheter at various locations. For example, the piezo-electric materials can be provided (i) in or on the outer surface of the outer layer, (ii) in or on the inner surface of the inner layer, (iii) between the inner layer and the outer layer, or (iv) integrated with the reinforcement structure. In addition, a single piezo-electric element, or multiple piezo-electric elements, can be provided at a location near the distal tip of the catheter, at a location near the middle portion of the catheter, or at the proximal portion of the catheter. In the case of multiple piezo-electric elements, they can be provided at a variety of locations along the catheter from the proximal end to the distal tip, for example, one piezo-electric element can be provided at the proximal end and another piezo-electric element can be provided at the distal tip, as described below.

If multiple piezo-electric elements are used in the catheter design, there may be no need for an external power source to apply electric energy to operate the piezo-electric element(s). One or more piezo-electric materials itself can be used as the source to apply electric energy to other piezo-electric elements due to the fact that squeezing or deforming the piezo-electric material can generate electric energy, with the electric energy used to deform or bend other piezo-electric elements. For example, a piezo-electric element at a location near the proximal end of the catheter shaft can generate electric energy which can flow through a connecting wire a distal piezo-electric element to cause the distal tip to bend or deform.

FIGS. 1-4D illustrate one embodiment of a catheter according to the present invention. Referring to FIG. 1, the catheter 10 has a shaft 12 that has a distal end 14 and a proximal end that terminates at a hub 16.

Figure 4A:
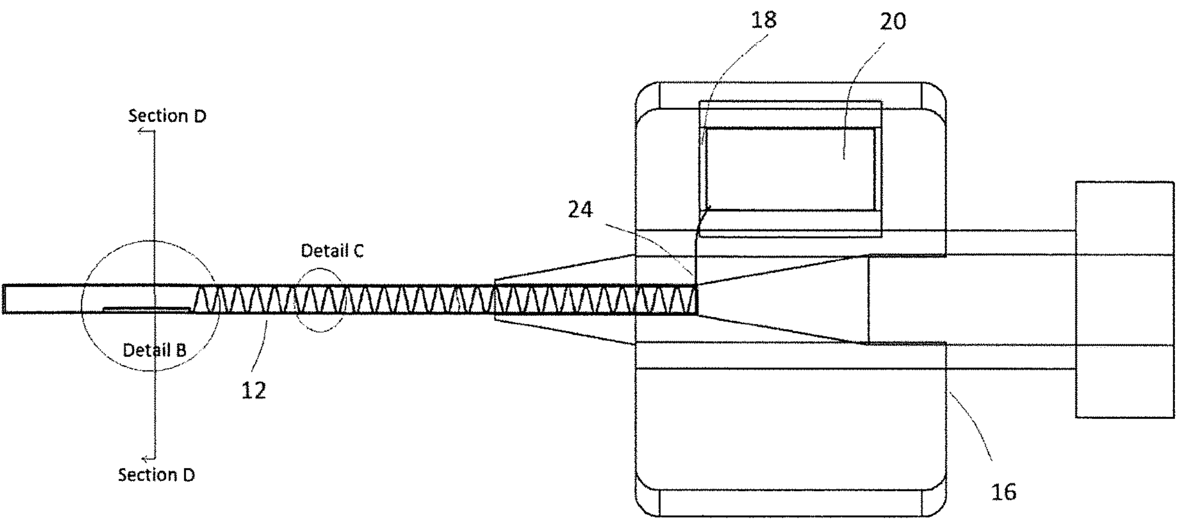
FIG. 4A is a further enlarged schematic view of the proximal end shown in FIG. 2A.
Figure 4B:
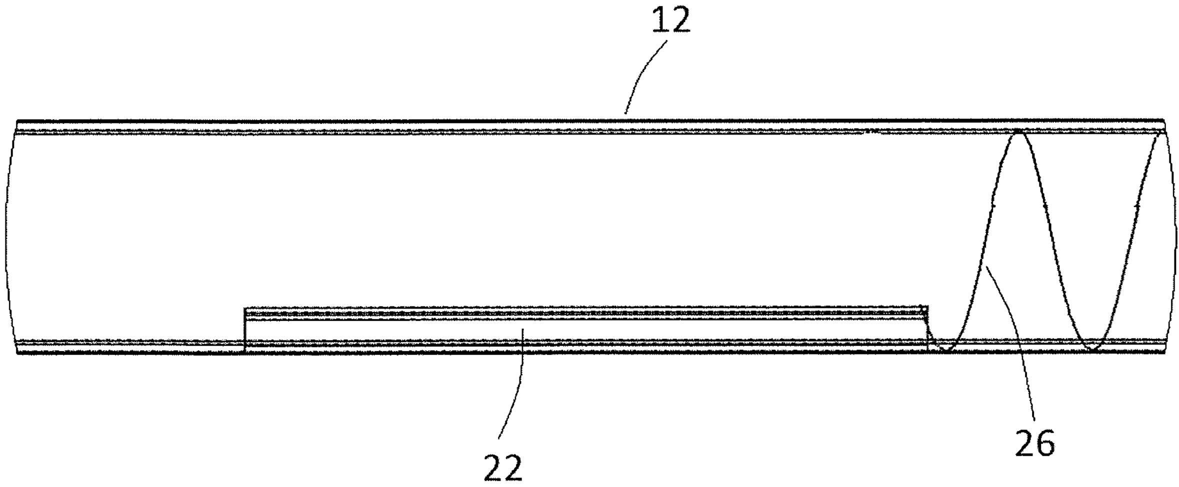
FIG. 4B is an enlarged side view of the region labeled "Detail B" in FIG. 4A.
Figure 4C:
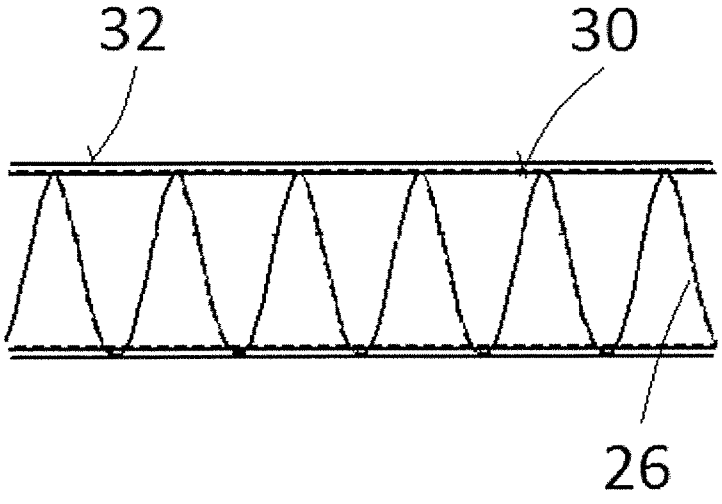
FIG. 4C is an enlarged view of the region labeled "Detail C" in FIG. 4A.
Figure 4D:
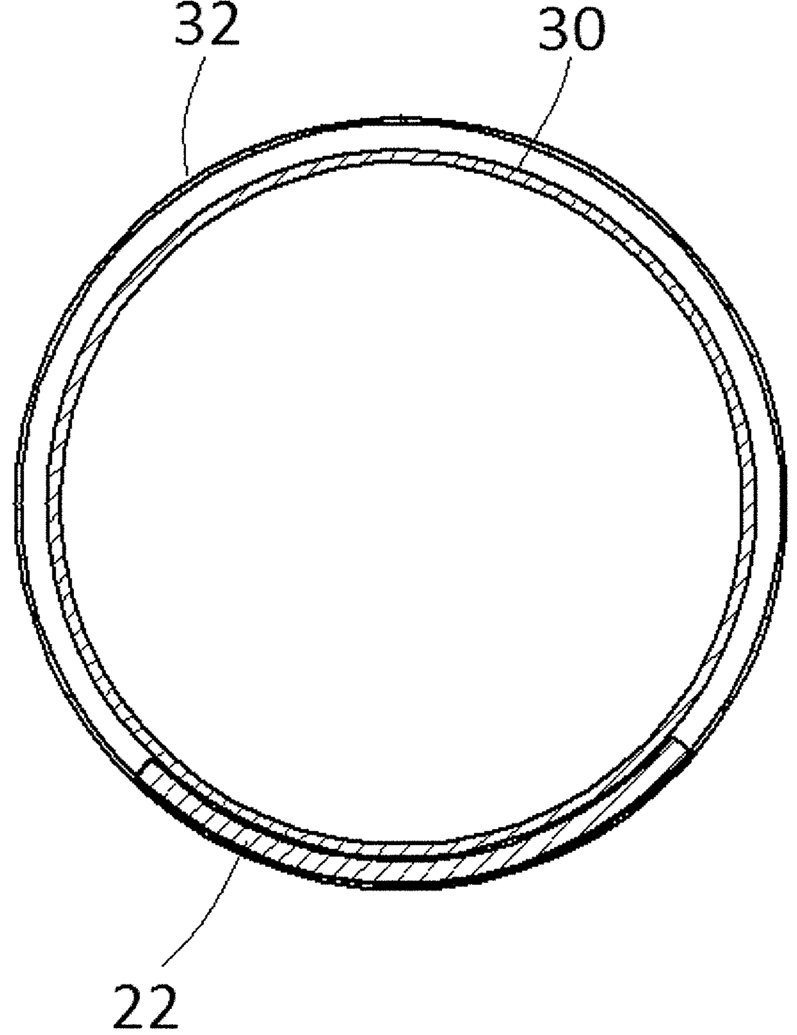
FIG. 4D is a cross-sectional view of the catheter taken along line "Section D-D" of FIG. 4A.

The construction of the shaft 12 is best illustrated in FIGS. 4C and 4D. The shaft 12 can have an inner layer 30 and an outer layer 32 which can be embodied in the same construction and materials as for those in conventional catheter shafts. The distal piezo-electric element 22 can be embedded between the inner layer 30 and the outer layer 32. The outer layer 32 and the inner layer 30 can be made from the same or different polymer materials with varying durometers (hardness). The inner layer 30 is preferably made from polymer materials with better lubricious properties, such as PTFE, so as to make the inner lumen surface lubricious and easier to deliver the treatment devices. Alternatively, an additional thin inner liner made from lubricious polymer materials can be bonded onto the inner layer to provide lubricity.

Figure 5:
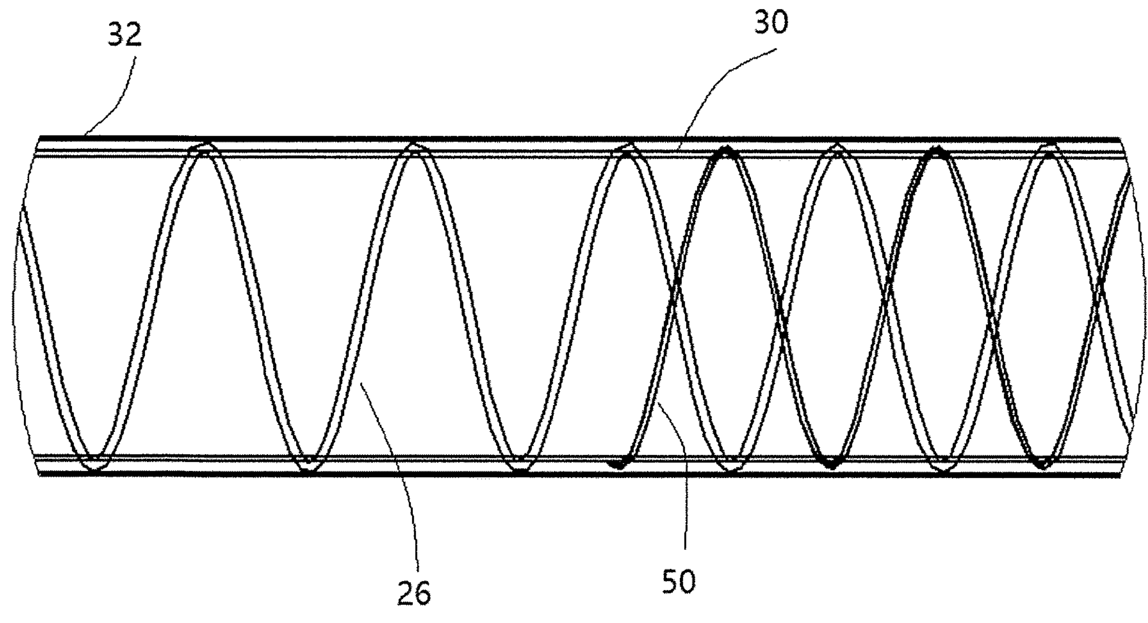
FIG. 5 illustrates a modification that can be made to the region shown in FIG. 4C.

As shown in FIG. 5, a reinforcement structure 50 can be embedded into the shaft 12 in a manner that is well known in the art. The reinforcement structure 50 can be a coiled or braided configuration. The conductive wire 26 can track along with the reinforcement structure 50 in the same configuration (not shown), or can be embedded separately from reinforcement structure 50, as shown in FIG. 5. It is also possible to use the conductive wire 26 as the reinforcement structure alone.

Figure 2A:
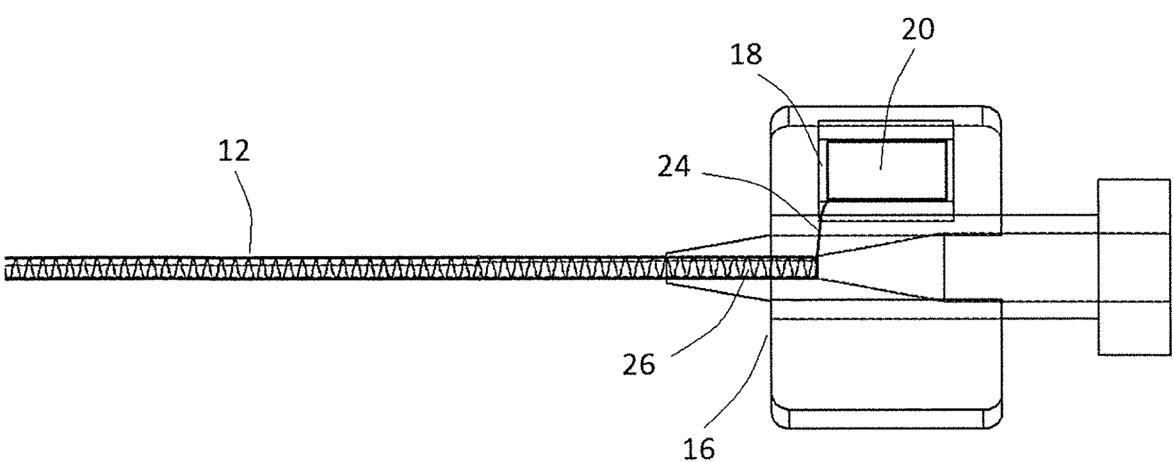
FIG. 2A is an enlarged schematic view of the proximal end of the catheter of FIG. 1.
Figure 2B:
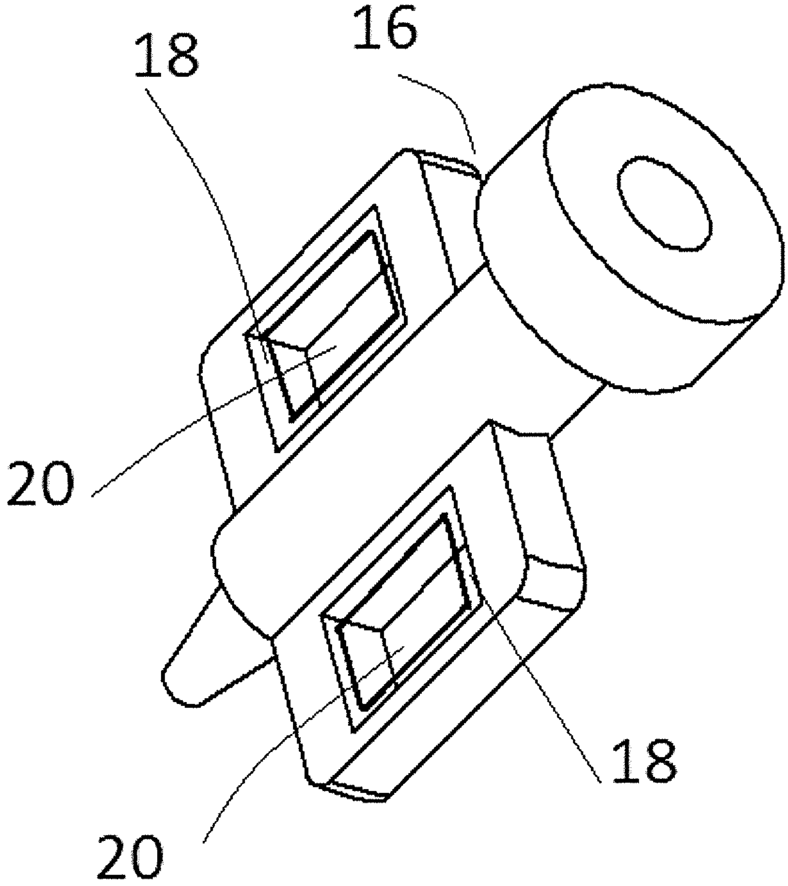
FIG. 2B is an enlarged view of the hub of the proximal end of the catheter of FIG. 1 showing more than one proximal piezo-electric element.

The hub 16 is shown in greater detail in FIGS. 2A and 2B. The hub 16 can have the features and construction of any conventional catheter hub, but it also includes at least one window 18 that houses or retains a proximal piezo-electric element 20. FIG. 2B shows that the hub 16 can have two windows 18, each housing a separate proximal piezo-electric element 20. The provision of two piezo-electric elements 20 allows for the generation of different polarity. For example, each piezo-electric element 20 can be configured to produce a different polarity, which will allow for more precise control of the movement or bend direction of the distal end 14 via the distal piezo-electric element 22. The polarity of the electric potential generated by piezoelectric materials depends on the direction of the mechanical stress applied to them. As a result of the different polarity, the distal end 14 can be deformed in different directions via the distal piezo-electric element 22.

Figure 3:
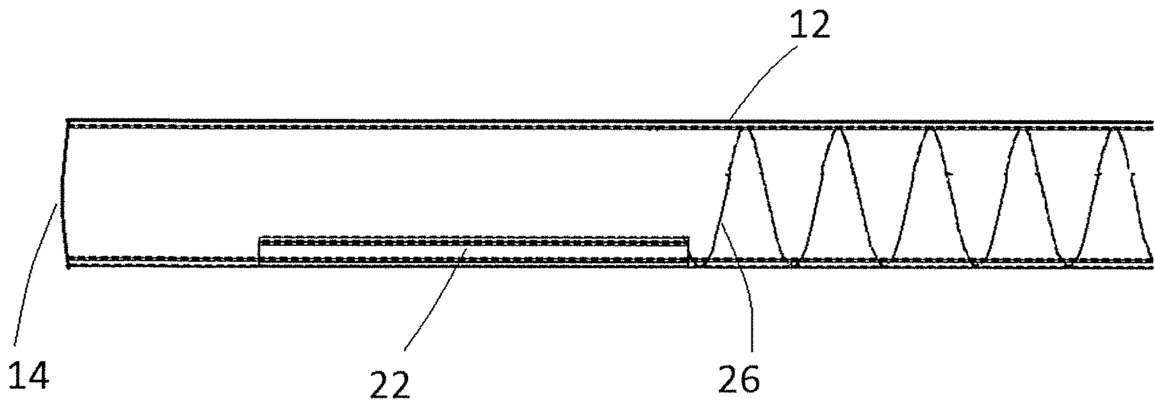
FIG. 3 is an enlarged schematic view of the distal end of the catheter of FIG. 1.

Connecting wires 24 connect the proximal piezo-electric element(s) 20 with a conductive wire 26 which connects to the distal piezo-electric element 22 (see FIG. 3 and FIGS. 4A-4B). The connecting wire(s) 24 can be embedded between the outer layer 32 and the inner layer 30 of the shaft 12 through a heat lamination process. When the distal piezo-electric element 22 senses an electrical current or potential from the conductive wire 26, it can bend or move accordingly, thereby causing the distal end 14 to bend or move.

Mechanical compression or tension on a poled piezoelectric material element changes the dipole moment, creating a voltage. Compression along the direction of polarization, or tension perpendicular to the direction of polarization, generates voltage of the same polarity as the poling voltage. Tension along the direction of polarization, or compression perpendicular to the direction of polarization, generates a voltage with polarity opposite that of the poling voltage. This is how the polarity is controlled by deforming the proximal piezo-electric element in a different manner. These actions are generator actions—the proximal piezo-electric element converts the mechanical energy of compression or tension into electrical energy. The electrical energy created then generates mechanical energy in the distal piezo-electrical element. Values for compressive stress and the voltage (or field strength) generated by applying stress to the proximal piezoelectric element are linearly proportional up to a material-specific stress. The same is true for applied voltage and generated strain.

If a voltage of the same polarity as the poling voltage is applied to the distal piezo-electric element, in the direction of the poling voltage, the element will lengthen and its diameter will become smaller. If a voltage of polarity opposite that of the poling voltage is applied, the element will become shorter and broader. This is how the bend/deformation direction of the distal piezo-electric element can be controlled, and hence of the movement of the distal tip/end of the catheter.

If an alternating voltage is applied by applying the alternating mechanical energy to the proximal piezo-electric element, the distal piezo-electric element will lengthen and shorten cyclically, at the frequency of the applied voltage. This is the action can make the catheter tip “move like snake” to make the navigation easier.

Electric potential can be generated by squeezing or deforming the proximal piezo-electric element 20 by compressing the proximal piezo-electric element 20 by using one’s hand. The electricity generated by the proximal piezo-electric element flows through the conductive wires 26 to the distal piezo-electric element 22. The distal piezo-electric element 22 will be bent or deformed by the electric field, hence bending the catheter tip. If needed, a rectifier bridge may be used for full-wave rectification.

Figure 6:
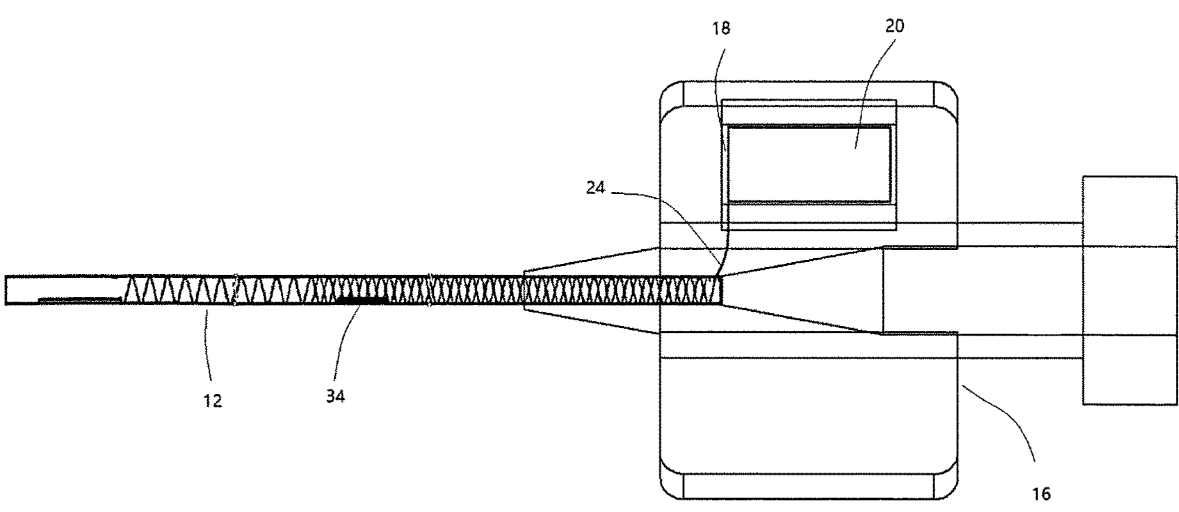
FIG. 6 is a schematic view of a catheter according to another embodiment of the present invention.

As shown in FIG. 6, additional intermediate piezo-electric elements 34 can be provided in the shaft 12 at intermediate locations, such as near expected bend locations in the shaft 12 that will be adjacent expected bend locations in the vasculature.

Actuating (e.g., squeezing or deforming the proximal piezo-electric element as described above) is not the only way to eliminate the need for an external electric energy source. For example, electric potential can also be generated from the deformation of the intermediate piezo-electric element 34 to operate the distal piezo-electric element 22. The deformation of the intermediate piezo-electric material 34 can be achieved during the navigation process of the catheter. For example, when intermediate piezo-electric material 34 passes a bend location in the vasculature, it will be deformed, thereby producing electric potential in the same manner described above to generate current flow to distal piezo-electric element 22.

The catheter design/construction disclosed in the present invention can be used either as an access catheter (e.g., sheath, guide catheter, intermediate catheter, microcatheter, distal access catheters, etc.), or as a treatment catheter, such as an aspiration catheter for stroke treatment, aspiration catheters for clot management in other vasculatures, etc. The catheters of the present invention can be used to access any human vasculature, including neuro, peripheral, and coronary locations to deliver the treatment device or other medical therapies. The catheter can also be used in both arteries and veins, and other body lumens, to deliver the treatment device or medical therapies.

The catheter according to the present invention can potentially reduce the number of steps during a procedure as a fewer number of access catheters are needed, thereby reducing the procedure time. For example, intermediate catheters, or distal access catheters, may not be needed in the procedure to help an aspiration catheter to navigate to the target location in the vasculature.

The catheter according to the present invention can also improve trackability and pushability of the catheter.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method of advancing a catheter within a human vessel, comprising:

providing a catheter having:
- a shaft that has a distal end and a proximal end;
- a hub provided at the proximal end, with a first piezo-electric element provided at the hub;
- a second piezoelectric element provided at a location on the shaft that is distal to the hub; and
- a conductive wire connecting the first piezoelectric element and the second piezoelectric element; and applying electrical energy from the first piezoelectric element towards the second piezoelectric element to cause the distal end of the shaft to move.

2. The method of claim 1, further including providing the first piezoelectric element and the second piezoelectric element from either a piezo-electric ceramic material, or a ferroelectric material, or a piezo-electric polymer material, or a composite material made from piezo-electric ceramic material and piezo-electric polymer material.

3. The method of claim 1, wherein each of the first piezoelectric element and the second piezoelectric element provides a source of electric energy.

4. The method of claim 1, further providing a third piezoelectric element positioned along the shaft between the first piezoelectric element and the second piezoelectric element.

* * * * *